United States Patent
Dong

(10) Patent No.: US 10,335,090 B2
(45) Date of Patent: Jul. 2, 2019

(54) MOBILE PHONE HOLDER FOR MONITORING PHYSICAL FEATURE AND PHYSICAL FEATURE MONITORING METHOD

(71) Applicant: BOE TECHNOLOGY GROUP CO., LTD., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/966,289

(22) Filed: Apr. 30, 2018

(65) Prior Publication Data

US 2019/0090817 A1 Mar. 28, 2019

(30) Foreign Application Priority Data

Sep. 27, 2017 (CN) .......................... 2017 1 0895832

(51) Int. Cl.
*A61B 5/00* (2006.01)
*A61B 5/024* (2006.01)
*A61B 5/1172* (2016.01)
*G06K 9/00* (2006.01)

(52) U.S. Cl.
CPC ........ *A61B 5/6898* (2013.01); *A61B 5/02416* (2013.01); *A61B 5/02438* (2013.01); *A61B 5/1172* (2013.01); *A61B 5/486* (2013.01); *A61B 5/7445* (2013.01); *A61B 2562/0247* (2013.01); *G06K 9/00087* (2013.01)

(58) Field of Classification Search
None
See application file for complete search history.

(56) References Cited

U.S. PATENT DOCUMENTS

| | | | | |
|---|---|---|---|---|
| 8,554,292 B1* | 10/2013 | Alsaffar | ................ | H04M 1/04 455/575.4 |
| 8,622,447 B1* | 1/2014 | Wirtz | .................... | H04B 1/385 224/217 |
| 2003/0190062 A1* | 10/2003 | Noro | ...................... | A61B 5/022 382/124 |
| 2011/0144918 A1* | 6/2011 | Inoue | ................. | A61B 5/02225 702/19 |
| 2011/0208068 A1* | 8/2011 | Ariga | .................. | A61B 5/02233 600/490 |
| 2012/0123281 A1* | 5/2012 | Ashida | ............... | A61B 5/02141 600/499 |
| 2013/0279098 A1* | 10/2013 | Cho | ........................ | H05K 7/00 361/679.01 |
| 2014/0027482 A1* | 1/2014 | Crawford | ............... | A45F 5/102 224/197 |
| 2014/0347491 A1* | 11/2014 | Connor | ................. | A61B 5/1114 348/158 |

(Continued)

*Primary Examiner* — Zhiyu Lu
(74) *Attorney, Agent, or Firm* — Brooks Kushman P.C.

(57) ABSTRACT

A mobile phone holder for monitoring a physical feature and a physical feature monitoring method are provided. The mobile phone holder includes an annular member and a base connected to the annular member. The annular member is configured to collect physical feature data of a user, and the base is configured to acquire a physical feature parameter in accordance with the physical feature data, and control to display the physical feature parameter.

15 Claims, 4 Drawing Sheets

(56) References Cited

U.S. PATENT DOCUMENTS

| | | | |
|---|---|---|---|
| 2014/0349256 A1* | 11/2014 | Connor | G09B 19/0092 434/127 |
| 2014/0349257 A1* | 11/2014 | Connor | G09B 19/0092 434/127 |
| 2015/0126873 A1* | 5/2015 | Connor | A61B 5/4866 600/475 |
| 2015/0168365 A1* | 6/2015 | Connor | G01N 33/02 356/51 |
| 2015/0182160 A1* | 7/2015 | Kim | A61B 5/0488 600/301 |
| 2016/0034764 A1* | 2/2016 | Connor | G06K 9/00771 348/158 |
| 2016/0073886 A1* | 3/2016 | Connor | G09B 19/0092 600/475 |
| 2016/0112684 A1* | 4/2016 | Connor | G01N 33/02 348/158 |
| 2016/0140870 A1* | 5/2016 | Connor | G09B 19/0092 356/51 |
| 2016/0317060 A1* | 11/2016 | Connor | G01J 3/0294 |
| 2017/0164878 A1* | 6/2017 | Connor | A61B 5/14532 |
| 2018/0220782 A1* | 8/2018 | Mody | A45F 5/00 |
| 2018/0228280 A1* | 8/2018 | Li | B65D 81/36 |
| 2018/0235468 A1* | 8/2018 | Khachaturian | A61B 5/02427 |

* cited by examiner

MOBILE PHONE HOLDER FOR MONITORING PHYSICAL FEATURE AND PHYSICAL FEATURE MONITORING METHOD

CROSS-REFERENCE TO RELATED APPLICATION

This application claims priority to Chinese Patent Application No. 201710895832.8 filed on Sep. 27, 2017, which is incorporated herein by reference in its entirety.

TECHNICAL FIELD

The present disclosure relates to the field of medical care, in particular to a mobile phone holder for monitoring a physical feature and a physical feature monitoring method.

BACKGROUND

For a noninvasive physical feature detection device in the related art, it is able to detect multiple physical features, e.g., blood pressure, pulse, oxygen saturation, hematocrit value, pH value and blood viscosity, of a user in a noninvasive manner through detecting a hand of the user.

However, the device needs to be carried by the user individually and cooperate with a mobile phone, so as to display the physical features through the mobile phone. In addition, during the detection, the device needs to be hold by the hand, so the convenience and the efficiency may be adversely affected.

SUMMARY

In one aspect, the present disclosure provides in some embodiments a mobile phone holder for monitoring a physical feature of a user, including a first body and a base connected to the first body. The first body is configured to collect physical feature data of the user, and the base is configured to determine a physical feature parameter of the user in accordance with the physical feature data, and control to display the physical feature parameter.

In a possible embodiment of the present disclosure, the base is further configured to determine health prompt information in accordance with the physical feature parameter, and control to display the health prompt information.

In a possible embodiment of the present disclosure, the first body includes an annular body, a collection circuit arranged at an inner side of the annular body, and a transmission circuit arranged between the annular body and the collection circuit. The collection circuit is configured to collect the physical feature data of the user, and the transmission circuit is configured to transmit the physical feature data collected by the collection circuit to the base.

In a possible embodiment of the present disclosure, the collection circuit includes a pressure sensor and an optical physical feature detection sensor.

In a possible embodiment of the present disclosure, the base includes a base body, a display panel arranged at a surface of the base body, and a first processing circuit and a driving circuit arranged within the base body. The first processing circuit is configured to acquire the physical feature data, determine the physical feature parameter in accordance with the physical feature data, determine the health prompt information in accordance with the physical feature parameter, and control the driving circuit to display the physical feature parameter and the health prompt information. The driving circuit is configured to drive the display panel to display the physical feature parameter and the health prompt information.

In a possible embodiment of the present disclosure, the first processing circuit includes an acquisition circuit and a second processing circuit. The acquisition circuit is configured to acquire the physical feature data and/or the health prompt information returned from a server. The second processing circuit is configured to convert and analyze the physical feature data to acquire the physical feature parameter, and further configured to compare the physical feature parameter currently acquired by the acquisition circuit with a predetermined physical feature parameter and/or a historical physical feature parameter to acquire the health prompt information, and/or transmit the physical feature parameter to the server.

In a possible embodiment of the present disclosure, the base further includes: a fingerprint collection circuit arranged at the surface of the base body and configured to collect fingerprint data of the user.

In a possible embodiment of the present disclosure, the second processing circuit is further configured to match the fingerprint data with predetermined fingerprint data to identify the user.

In a possible embodiment of the present disclosure, the base further includes: a pulse detection circuit arranged at a surface of the fingerprint collection circuit, and configured to collect a pulse wave of the user in the case that the fingerprint data of the user is being collected by the fingerprint collection circuit.

In a possible embodiment of the present disclosure, the base further includes: an adjustment button arranged at the surface of the base body, and configured to adjust a content displayed on the display panel and a display effect of the content.

In a possible embodiment of the present disclosure, the first body is of an annular shape.

In a possible embodiment of the present disclosure, the collection circuit further includes a pulse wave sensor.

In another aspect, the present disclosure provides in some embodiments the physical feature monitoring method implemented by the mobile phone holder for monitoring the physical feature, including steps of: acquiring the physical feature data of the user; and determining a physical feature parameter of the user in accordance with the physical feature data, and controlling to display the physical feature parameter.

In a possible embodiment of the present disclosure, the physical feature monitoring method further includes: determining health prompt information in accordance with the physical feature parameter, and controlling to display the health prompt information.

In a possible embodiment of the present disclosure, the step of determining the physical feature parameter of the user in accordance with the physical feature data includes: converting and analyzing the physical feature data to acquire the physical feature parameter.

In a possible embodiment of the present disclosure, the step of determining the health prompt information in accordance with the physical feature parameter includes: comparing the currently-determined physical feature parameter with a predetermined physical feature parameter and/or a historical physical feature parameter to acquire the health prompt information, and/or transmitting the physical feature parameter to a server and acquiring the health prompt information returned from the server.

In a possible embodiment of the present disclosure, prior to the step of acquiring the physical feature data of the user, the physical feature monitoring method further includes acquiring fingerprint data of the user, and matching the fingerprint data with predetermined fingerprint data to identify the user.

BRIEF DESCRIPTION OF THE DRAWINGS

In order to illustrate the technical solutions of the present disclosure in a clearer manner, the drawings desired for the present disclosure will be described hereinafter briefly. Obviously, the following drawings merely relate to some embodiments of the present disclosure, and based on these drawings, a person skilled in the art may obtain the other drawings without any creative effort.

DETAILED DESCRIPTION

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

Figure 1:
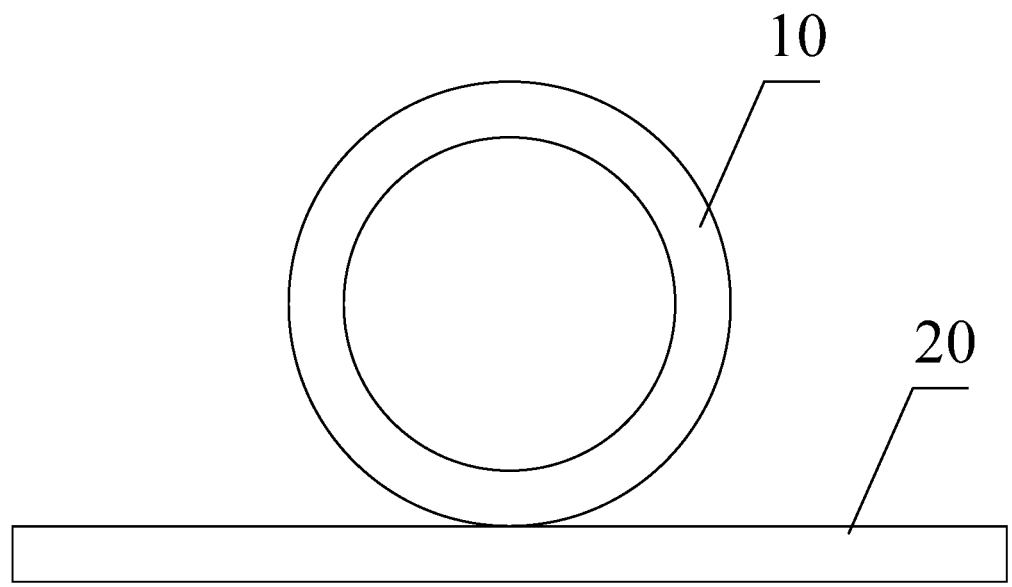
FIG. 1 is a side view of a mobile phone holder for monitoring a physical feature according to one embodiment of the present disclosure.

The present disclosure provides in some embodiments a mobile phone holder for monitoring a physical feature. As shown in FIG. 1, which is a side view of the mobile phone holder, the mobile phone holder includes an annular member 10 and a base 20 connected to the annular member 10. The annular member 10 is configured to collect physical feature data of a user. The base 20 is configured to determine a physical feature parameter of the user in accordance with the physical feature data, and display the physical feature parameter.

To be specific, the annular member 10 is capable of allowing a finger of the user to be inserted through and being rotated by 360°, so as to facilitate the user to hold the mobile phone, thereby to be adapted to different fingers and a holding angle of each finger. In addition, the annular member 10 may be angled relative to a surface of the mobile phone at any angle or entirely attached onto the plane of the base. The annular member 10 may be made of a material such as rubber or plastics. A size of the annular member 10 may be determined in accordance with the practical need. Of course, a material, a shape and the size of the annular member will not be particularly defined herein.

To be specific, the base 20 is further connected to a housing of the mobile phone. The base 20 may be made of a material such as rubber or plastics, and has a rectangular, cylindrical shape, or etc. A size of the base 20 may be determined in accordance with the practical need. Of course, the material, the shape and the size of the base will not be particularly defined herein.

A connection mode between the annular member 10 and the base 20 is known in the art, and thus will not be particularly defined herein.

To be specific, the physical feature parameter may include blood pressure, peripheral pulse, oxygen saturation, hemoglobin concentration, carbon dioxide partial pressure, oxygen partial pressure, mean pulsating pressure, cardiac output, stroke volume, total carbon dioxide concentration, oxygen content, hematocrit, red blood cell count, pH value or blood viscosity.

According to the embodiments of the present disclosure, the mobile phone holder for monitoring the physical feature includes the annular member and the base connected to the annular member. The annular member is configured to collect the physical feature data of the user. The base is configured to determine the physical feature parameter of the user in accordance with the physical feature data, and display the physical feature parameter. A physical feature monitoring function is integrated into the mobile phone holder, so the physical feature of the user may be monitored in the case of holding the mobile phone by the hand of the user, and it is unnecessary for the user to carry a physical feature monitoring device individually, thereby to increase the convenience and the efficiency.

In a possible embodiment of the present disclosure, the base 20 is further configured to determine health prompt information in accordance with the physical feature parameter and display the health prompt information.

The health prompt information may include a current health state of the user, e.g., a health state, a sub-health state, or a sick state, and/or issues to be paid attention to, such as diet or sleep.

According to the embodiments of the present disclosure, the health prompt information may be acquired and displayed, so as to intuitively prompt the user of the current health state and the issues to be paid attention to, so as to facilitate the use of the mobile phone holder.

Figure 2:
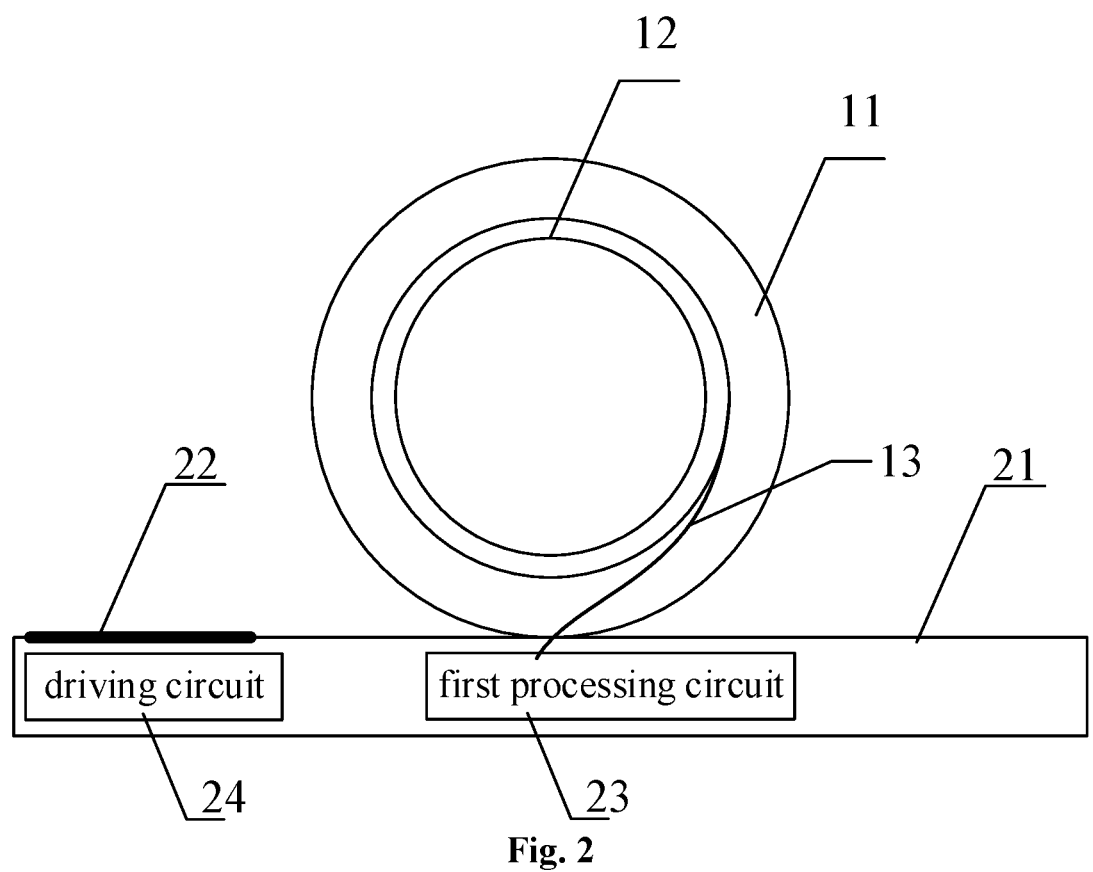
FIG. 2 is another side view of the mobile phone holder for monitoring the physical feature according to one embodiment of the present disclosure.
Figure 3:
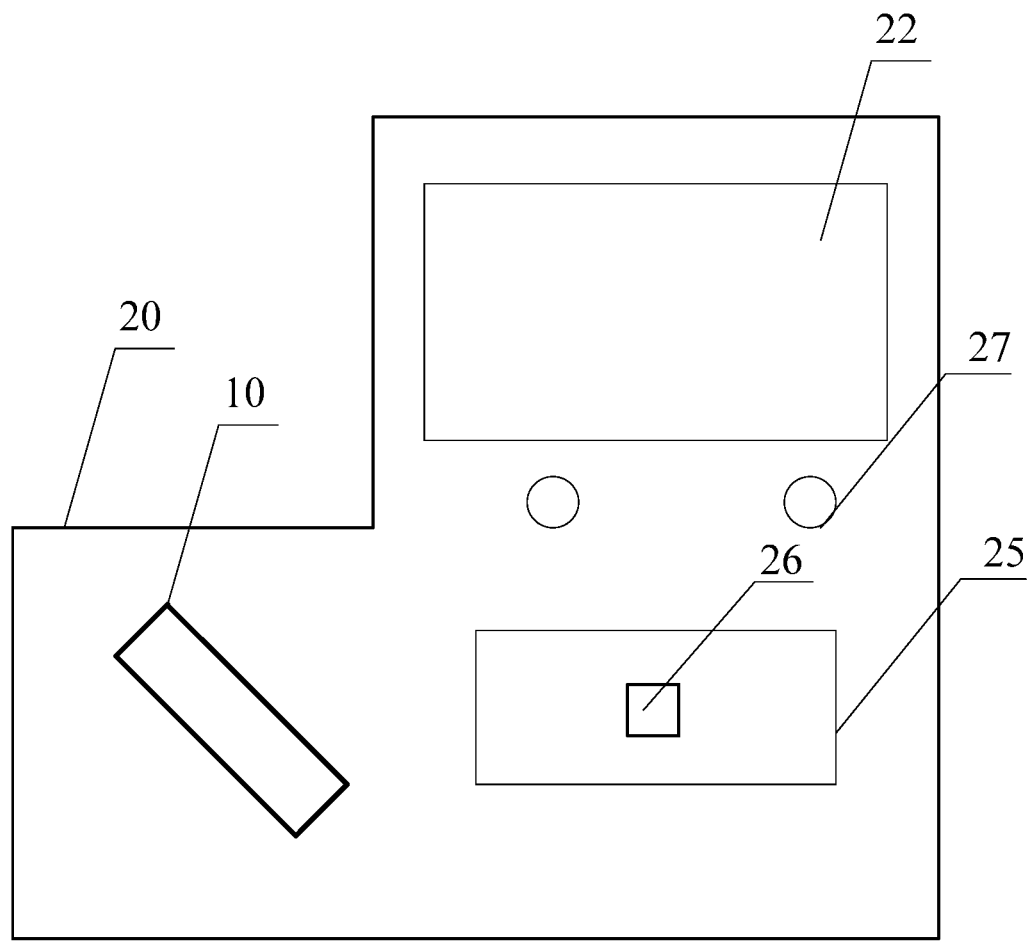
FIG. 3 is a top view of the mobile phone holder for monitoring the physical feature according to one embodiment of the present disclosure.

FIG. 2 is another side view of the mobile phone holder for monitoring the physical feature, and FIG. 3 is a top view of the mobile phone holder for monitoring the physical feature. As shown in FIG. 2, the annular member includes an annular body 11, a collection circuit 12 arranged at an inner side of the annular body, and a transmission circuit 13 arranged between the annular body 11 and the collection circuit 12.

To be specific, the collection circuit 12 is configured to collect the physical feature data of the user, and the transmission circuit 13 is configured to transmit the physical feature data collected by the collection circuit to the base 20.

Figure 7:
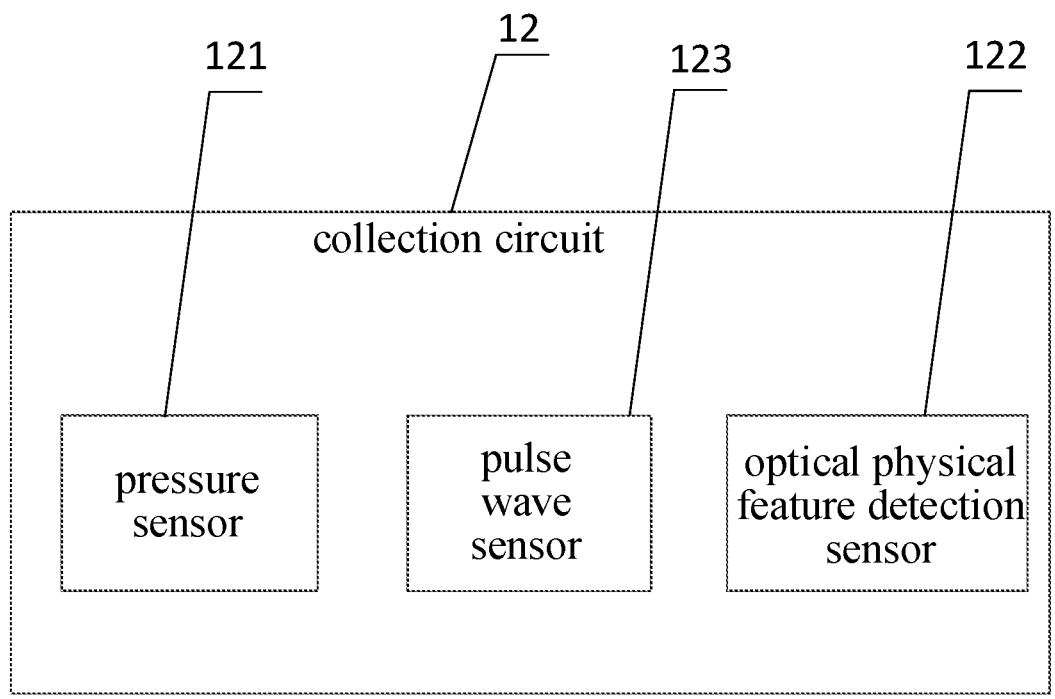
FIG. 7 is a schematic view showing a collection circuit according to one embodiment of the present disclosure.

In a possible embodiment of the present disclosure, as shown in FIG. 7, the collection circuit 12 includes a pressure sensor 121 and an optical physical feature detection sensor 122.

To be specific, the pressure sensor 121 is configured to collect blood pressure data of the user, and the optical physical feature detection sensor 122 is configured to collect a heart rate or any other physical feature data of the user. It should be appreciated that, the optical physical feature detection sensor 122 includes a light plethysmograph for detecting the heart rate or any other physical feature data of the user. The light plethysmograph includes at least one laser source and at least one photoelectric detector. A light beam from the laser source is directed to a skin of the user, and the light beam reflected by the skin is capable of being detected by the photoelectric detector. In addition, the collection circuit 12 may further include any other sensor capable of collecting the physical feature data of the user, e.g., a pulse wave sensor 123, which will not be particularly defined herein.

In a possible embodiment of the present disclosure, the transmission circuit 13 is a signal sensing line connected to the collection circuit 12 and the base 20.

As shown in FIGS. 2 and 3, the base includes a base body 21, a display panel 22 arranged at a surface of the base body 21, and a first processing circuit 23 and a driving circuit 24 arranged within the base body 21.

The first processing circuit 23 is configured to acquire the physical feature data, determine the physical feature parameter in accordance with the physical feature data, and determine the health prompt information in accordance with the physical feature parameter and control the driving circuit to display the physical feature parameter and the health prompt information. In a possible embodiment of the present disclosure, the first processing circuit 23 may be a microprocessor.

The driving circuit 24 is configured to drive the display panel 22 to display the physical feature parameter and the health prompt information. In a possible embodiment of the present disclosure, the display panel 22 is a liquid crystal display.

Figure 4:
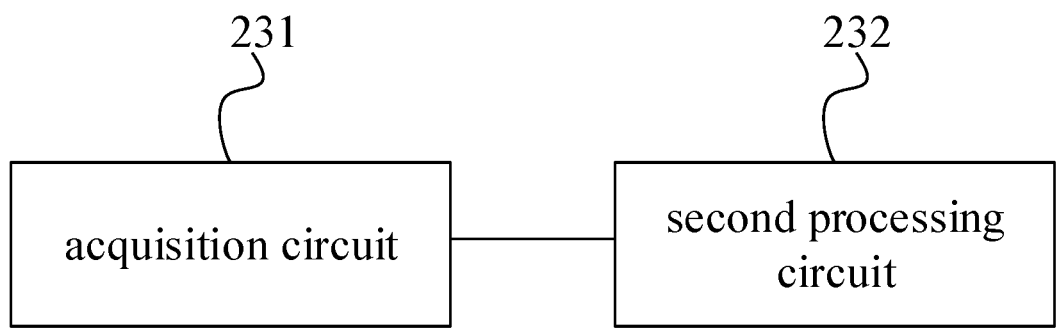
FIG. 4 is a schematic view showing a first processing circuit according to one embodiment of the present disclosure.

As shown in FIG. 4, which is a schematic view showing the first processing circuit, the first processing circuit includes an acquisition circuit 231 and a second processing circuit 232. The acquisition circuit 231 is configured to acquire the physical feature data and/or the health prompt information returned from a server. The second processing circuit 232 is configured to convert and analyze the physical feature data so as to acquire the physical feature parameter, and further configured to compare the physical feature parameter currently acquired by the acquisition circuit with a predetermined physical feature parameter and/or a historical physical feature parameter so as to acquire the health prompt information, and/or transmit the physical feature parameter to the server.

It should be appreciated that, a large-scale server may be provided by a manufacturer of the mobile phone holder. In the case that the physical feature parameter is transmitted to the server, it may be analyzed by the server so as to acquire the health prompt information.

To be specific, an analog signal is acquired by the acquisition circuit 231, and the second processing circuit 232 is configured to convert the analog signal into a digital signal, and analyze the digital signal so as to acquire the physical feature parameter.

As shown in FIG. 3, the base further includes a fingerprint collection circuit 25 arranged at the surface of the base body 21 and configured to collect fingerprint data of the user. The second processing circuit 232 is further configured to match the fingerprint data with predetermined fingerprint data, so as to identify the user.

In the case that the fingerprint data successfully matches the predetermined fingerprint data, it is able to acquire the historical physical feature parameter of the user corresponding to the predetermined fingerprint data. In the case that the fingerprint data fails to successfully match the predetermined fingerprint data, it is unnecessary to collect the physical feature data of the user, or the fingerprint data may be stored and determined as being from a new user.

In a possible embodiment of the present disclosure, the base further includes a pulse detection circuit 26 arranged at a surface of the fingerprint collection circuit 25 and configured to collect a pulse wave of the user in the case that the fingerprint data of the user is being collected. In a possible embodiment of the present disclosure, the pulse detection circuit 26 is a pulse wave sensor.

It should be appreciated that, in the case that the pulse detection circuit is arranged at the surface of the fingerprint collection circuit 25, the collection circuit 12 of the annular member may not include the pulse wave sensor. In the case that no pulse detection circuit is arranged at the surface of the fingerprint collection circuit 25, the collection circuit 12 of the annular member may include the pulse wave sensor. In other words, it is merely necessary to provide the pulse wave sensor on one of the collection circuit and the fingerprint collection circuit.

In a possible embodiment of the present disclosure, the base further includes an adjustment button 27 arranged at the surface of the base body and configured to adjust a content displayed on the display panel 22 and a display effect of the content. To be specific, the user may rotate the adjustment button, so as to adjust the content displayed on the display panel and the display effect of the content.

In a possible embodiment of the present disclosure, the base further includes a power manager (not shown) connected to the first processing circuit and configured to supply power to the first processing circuit.

In a possible embodiment of the present disclosure, the base further includes an attachment member (not shown) arranged at a bottom of the base and configured to be connected to the mobile phone or the housing of the mobile phone.

Figure 5:
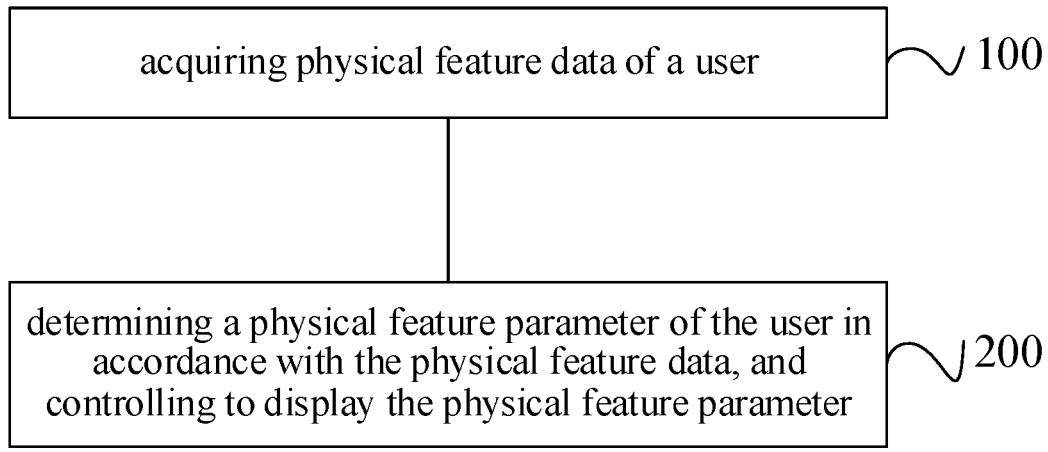
FIG. 5 is a flow chart of a physical feature monitoring method according to one embodiment of the present disclosure.

Based on an identical inventive concept, the present disclosure provides in some embodiments a physical feature monitoring method implemented by the above-mentioned mobile phone holder, which, as shown in FIG. 5, includes the following steps.

Step 100: acquiring physical feature data of a user. The physical feature data is an analog signal.

Step 200: determining a physical feature parameter of the user in accordance with the physical feature data, and controlling to display the physical feature parameter.

To be specific, Step 200 includes converting and analyzing the physical feature data, so as to acquire the physical feature parameter. To be specific, an analog signal may be converted into a digital signal.

To be specific, the physical feature parameter may include blood pressure, peripheral pulse, oxygen saturation, hemoglobin concentration, carbon dioxide partial pressure, oxygen partial pressure, mean pulsating pressure, cardiac output, stroke volume, total carbon dioxide concentration, oxygen content, hematocrit, red blood cell count, pH value or blood viscosity.

According to the embodiments of the present disclosure, the physical feature monitoring method implemented by the above-mentioned mobile phone holder includes steps of: acquiring the physical feature data of the user; and determining the physical feature parameter of the user in accordance with the physical feature data, and controlling to display the physical feature parameter. A physical feature monitoring function is achieved by the mobile phone holder, so the physical feature of the user may be monitored in the case of holding the mobile phone by the hand of the user, and it is unnecessary for the user to carry a physical feature monitoring device individually and hold the mobile phone by hand in the case of monitoring the physical feature, thereby to increase the convenience and the efficiency.

Figure 6:
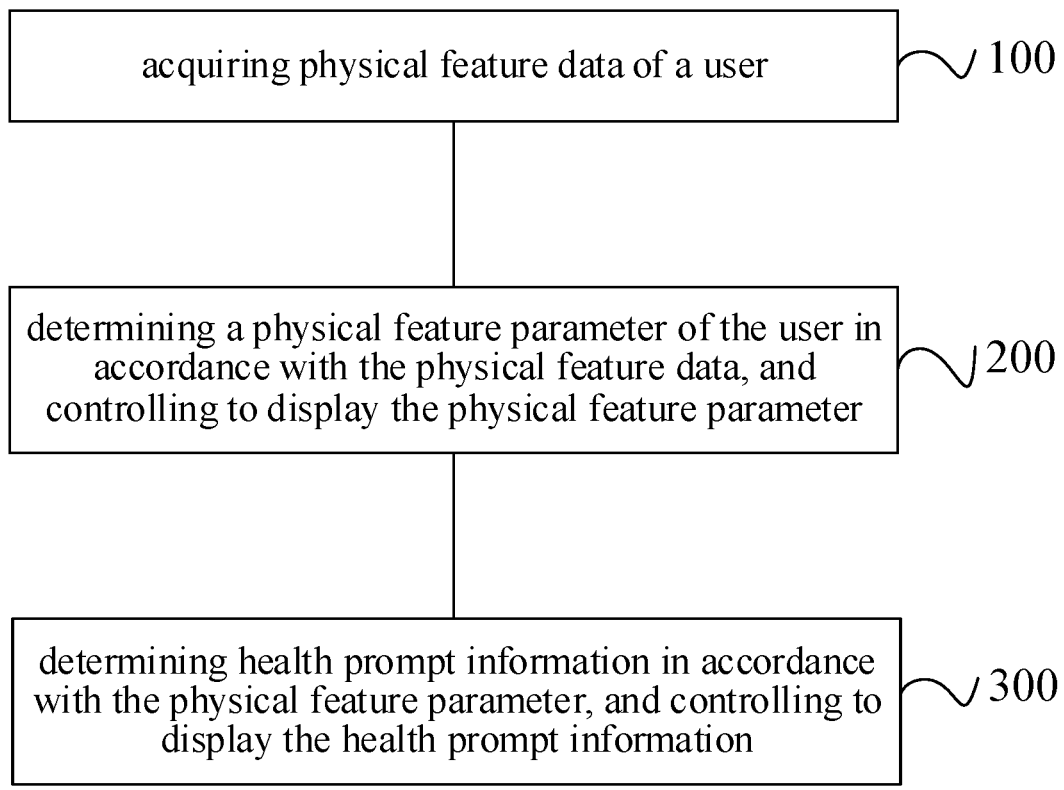
FIG. 6 is another flow chart of the physical feature monitoring method according to one embodiment of the present disclosure.

As shown in FIG. 6, which is another flow chart of the physical feature monitoring method, subsequent to Step 200, the physical feature monitoring method further includes Step 300 of determining health prompt information in accordance with the physical feature parameter, and controlling to display the health prompt information.

To be specific, Step 300 includes: comparing the currently-determined physical feature parameter with a predetermined physical feature parameter and/or a historical physical feature parameter so as to acquire the health prompt information, and/or transmitting the physical feature parameter to a server and acquiring the health prompt information returned from the server.

The health prompt information may include a current health state of the user, e.g., a health state, a sub-health state, or a sick state, and/or issues to be paid attention to, such as diet or sleep.

It should be appreciated that, a large-scale server may be provided by a manufacturer of the mobile phone holder. In the case that the physical feature parameter is transmitted to the server, it may be analyzed by the server so as to acquire the health prompt information.

According to the embodiments of the present disclosure, the health prompt information may be acquired and displayed, so as to intuitively prompt the user of the current health state and the issues to be paid attention to, so as to facilitate the use of the mobile phone holder.

In a possible embodiment of the present disclosure, prior to Step 100, the physical feature monitoring method further includes: acquiring fingerprint data of the user, and matching the fingerprint data with predetermined fingerprint data so as to identify the user.

It should be appreciated that, in the case that the fingerprint data successfully matches the predetermined fingerprint data, it is able to acquire the historical physical feature parameter of the user corresponding to the predetermined fingerprint data. In the case that the fingerprint data fails to successfully match the predetermined fingerprint data, it is unnecessary to collect the physical feature data of the user, or the fingerprint data may be stored and determined as being from a new user.

The physical feature monitoring method will be further described hereinafter.

The physical feature monitoring method includes steps of: acquiring the fingerprint data of the user; matching the fingerprint data with the predetermined fingerprint data, so as to identify the user; in the case that the fingerprint data successfully matching the predetermined fingerprint data, acquiring the physical feature data of the user; converting and analyzing the physical feature data so as to acquire the physical feature parameter; comparing the currently-acquired physical feature parameter with the predetermined physical feature parameter and/or the historical physical feature parameter so as to acquire the health prompt information, and/or transmitting the physical feature parameter to a server and acquiring the health prompt information from the server; and controlling to display the physical feature data and the health prompt information.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A mobile phone holder for monitoring a physical feature of a user, comprising a first body and a base,
   wherein the base is connected to the first body at a first side, and connected to a mobile phone at a second side, the first side of the base is opposite to a second side of the base, the first body is configured to collect physical feature data of the user, and the base is configured to determine a physical feature parameter of the user in accordance with the physical feature data, and control to display the physical feature parameter;
   the first body comprises an annular body, a collection circuit arranged at an inner side of the annular body, and a transmission circuit arranged between the annular body and the collection circuit, wherein the collection circuit is configured to collect the physical feature data of the user, and the transmission circuit is configured to transmit the physical feature data collected by the collection circuit to the base; and
   the first body is of an annular shape and comprises two toroidal surfaces being opposite to each other, and the first body is configured to be rotatable relative to the base, to enable either one of the two toroidal surfaces to be angled relative to a surface of the mobile phone at any angle in a range from 0 degree to 180 degrees.

2. The mobile phone holder according to claim 1, wherein the base is further configured to determine health prompt information in accordance with the physical feature parameter, and control to display the health prompt information.

3. The mobile phone holder according to claim 1, wherein the collection circuit comprises a pressure sensor and an optical physical feature detection sensor.

4. The mobile phone holder according to claim 2, wherein the base comprises a base body, a display panel arranged at a surface of the base body, and a first processing circuit and a driving circuit arranged within the base body,
   wherein the first processing circuit is configured to acquire the physical feature data, determine the physical feature parameter in accordance with the physical feature data, determine the health prompt information in accordance with the physical feature parameter, and control the driving circuit to display the physical feature parameter and the health prompt information; and
   the driving circuit is configured to drive the display panel to display the physical feature parameter and the health prompt information.

5. The mobile phone holder according to claim 4, wherein the first processing circuit comprises an acquisition circuit and a second processing circuit, wherein the acquisition circuit is configured to acquire the physical feature data and/or the health prompt information returned from a server; and the second processing circuit is configured to convert and analyze the physical feature data to acquire the physical feature parameter, and further configured to compare the physical feature parameter currently acquired by the acquisition circuit with a predetermined physical feature parameter and/or a historical physical feature parameter to acquire the health prompt information, and/or transmit the physical feature parameter to the server.

6. The mobile phone holder according to claim 5, wherein the base further comprises:

a fingerprint collection circuit arranged at the surface of the base body, and configured to collect fingerprint data of the user.

7. The mobile phone holder according to claim 6, wherein the second processing circuit is further configured to compare the fingerprint data with predetermined fingerprint data to identify the user.

8. The mobile phone holder according to claim 6, wherein the base further comprises:

a pulse detection circuit arranged at a surface of the fingerprint collection circuit, and configured to collect a pulse wave of the user in the case that the fingerprint data of the user is being collected by the fingerprint collection circuit.

9. The mobile phone holder according to claim 5, wherein the base further comprises:

an adjustment button arranged at the surface of the base body, and configured to adjust a content displayed on the display panel and a display effect of the content.

10. The mobile phone holder according to claim 3, wherein the collection circuit further comprises a pulse wave sensor.

11. A physical feature monitoring method implemented by a mobile phone holder for monitoring a physical feature of a user, wherein the mobile phone holder comprises a first body and a base, the base is connected to the first body at a first side and connected to a mobile phone at a second side, the first side of the base is opposite to a second side of the base, the first body is configured to collect physical feature data of the user, and the base is configured to determine a physical feature parameter of the user in accordance with the physical feature data, and control to display the physical feature parameter; the first body comprises an annular body, a collection circuit arranged at an inner side of the annular body, and a transmission circuit arranged between the annular body and the collection circuit, wherein the collection circuit is configured to collect the physical feature data of the user, and the transmission circuit is configured to transmit the physical feature data collected by the collection circuit to the base; and the first body is of an annular shape and comprises two toroidal surfaces being opposite to each other, and the first body is configured to be rotatable relative to the base, to enable either one of the two toroidal surfaces to be angled relative to a surface of the mobile phone at any angle in a range from 0 degree to 180 degrees, wherein the physical feature monitoring method comprises: acquiring the physical feature data of the user; and determining the physical feature parameter of the user in accordance with the physical feature data, and controlling to display the physical feature parameter.

12. The physical feature monitoring method according to claim 11, further comprising:

determining health prompt information in accordance with the physical feature parameter, and controlling to display the health prompt information.

13. The physical feature monitoring method according to claim 11, wherein the step of determining the physical feature parameter of the user in accordance with the physical feature data comprises:

converting and analyzing the physical feature data to acquire the physical feature parameter.

14. The physical feature monitoring method according to claim 12, wherein the step of determining the health prompt information in accordance with the physical feature parameter comprises:

comparing the currently-determined physical feature parameter with a predetermined physical feature parameter and/or a historical physical feature parameter to acquire the health prompt information, and/or transmitting the physical feature parameter to a server and acquiring the health prompt information returned from the server.

15. The physical feature monitoring method according to claim 11, wherein prior to the step of acquiring the physical feature data of the user, the physical feature monitoring method further comprises:

acquiring fingerprint data of the user; and comparing the fingerprint data with predetermined fingerprint data to identify the user.

\* \* \* \* \*